United States Patent [19]

Beck

[11] Patent Number: 5,436,276

[45] Date of Patent: Jul. 25, 1995

[54] METHOD FOR DETERMINING THE HARDNESS OF FRAGRANCE CONTAINING POLYURETHANE FOAMS

[75] Inventor: Charles E. J. Beck, Summit, N.J.

[73] Assignee: International Flavors & Fragrances Inc., New York, N.Y.

[21] Appl. No.: 149,782

[22] Filed: Nov. 10, 1993

[51] Int. Cl.$^6$ .................... C08G 18/08; A61K 7/46
[52] U.S. Cl. .................... 521/155; 436/106; 512/1; 512/4
[58] Field of Search .............. 512/4, 1; 436/106; 521/155

[56] References Cited

U.S. PATENT DOCUMENTS 4,842,761  6/1989  Rutherford .................. 512/4
5,238,915  8/1993  Fuwa et al. .................. 512/4

*Primary Examiner*—Nathan M. Nutter
*Assistant Examiner*—John M. Cooney, Jr.
*Attorney, Agent, or Firm*—Arthur L. Liberman

[57] ABSTRACT

A method is disclosed for controlling the hardness of a polyurethane foam by introducing an aroma chemical into the reaction mixture to form a polyurethane foam according to a desired hardness to be attained. The aroma chemical can be selected based on the empirical formula:

$$\log_e(\text{hardness of foam}) = 1.87(\text{polarity/molecular weight})^{0.27}$$

6 Claims, No Drawings

METHOD FOR DETERMINING THE HARDNESS OF FRAGRANCE CONTAINING POLYURETHANE FOAMS

INTRODUCTION AND BACKGROUND

The present invention relates to a method for predicting the structure and integrity of a polyurethane foam by means of the particular fragrance ingredient added to the reactant mixture. In another aspect, the present invention relates to a method for controlling the hardness of a polyurethane foam having a fragrance ingredient to produce a foam product with a desired degree of hardness ranging from soft to hard depending upon the selection of an aroma chemical which is introduced into the reaction mixture to form the polyurethane foam.

It is known in the past to produce polyurethane foams by introducing a fragrance component into the reactants to produce the polyurethane foam.

Such methods however have not been able to devise a way to predict and control the relative hardness of the resulting foam product by selecting and using a particular aroma chemical for incorporation into the foam producing formulation.

SUMMARY OF THE INVENTION

The present invention provides a method for predicting in advance the structure and integrity of a polyurethane foam by establishing a table of previously tested aroma chemicals according to observed relative hardness based on a given polyurethane foam forming composition and then selecting an aroma chemical based on the data in the table for inclusion into a selected formulation for producing a polyurethane foam of desired predictable properties.

In another aspect the invention provides a method of selecting an aroma chemical depending upon its polarity on a scale of 1 to 10 and actual molecular weight and predicting the approximate hardness of the resulting polyurethane foam based on establishing a range of hardness on a scale of from 1 to 10 for the resulting foam product, the maximum value of 10 indicating the highest degree of foam hardness.

In another aspect, the present invention provides a method for controlling the hardness of a polyurethane foam by selecting an aroma chemical, calculating the resulting hardness to be achieved according to an empirical formula and introducing the aroma chemical into the reaction mixture containing the polyurethane foam forming reactants to form the polyurethane foam according to the desired hardness to be attained. The empirical formula of the present invention is:

$$\log_e(Z) = 1.87(X/Y)^{0.27}$$

wherein
Z=hardness of foam on a scale of 1 to 10
X=polarity of aroma chemical on a scale of 1 to
Y=actual molecular weight of aroma chemical

DETAILED DESCRIPTION OF THE INVENTION

The polyurethane foams of the present invention are made by reacting an active-hydrogen containing compound, usually a polyol or mixtures of polyols, with a polyisocyanate or mixture of polyisocyanates. Optionally, extenders, blowing agents and the like which are conventional ingredients for preparing polyurethane foams also can be introduced into the reactant mixture.

The polyisocyanates which can be used for purposes of the present invention are modified and unmodified polyisocyanates which are well known to those skilled in art.

For the purposes of this invention the term polyisocyanate is used to describe compounds containing at least two isocyanate groups. Unmodified polyisocyanates included aliphatic or cycloaliphatic and aromatic polyisocyanates. Examples include 2,4- and 2,6-methylcyclohexylenediisocyanate, tetramethylene diisocyanante, cyclohexane diisocyanate, 2,4-toluene diisocyanate, 2,6-toluene diisocyanate, mixtures of 2,4- and 2,6-toluene diisocyanate, naphthalene-1,5-diisocyanante, 1-mexthoxyphenyl-2,4-diisocyanante. Preferred isocyanates include 4,4'-diphenylmethane diisocyanate (MDI), mixtures of 4,4- and 2,4-diphenylmethane diisocyanate, and polymeric polyisocyanates such as polymethylene polyphenylenes polyisocyanates (polymeric MDI).

These polyisocyanates are prepared by conventional methods known in the art, e.g. phosgenation of the corresponding organic amine.

For purposes of the present invention isocyanates other than the preferred isocyanates may be present in minor amounts.

In the preparation of the polyurethanes of the present invention the isocyanate is reacted with isocyanante reactive hydrogen-containing compounds (polyols are preferred). Hydroxyl group-containing compounds (polyols) useful in the preparation of polyurethanes are described in the Polyurethane Handbook in chapter 3, Section 3.1 pages 42–61; and in Polyurethanes; Chemistry and Technology in Chapter II, Sections III and IV, pages 32–47. Many hydroxyl-group containing compounds may be used, including simple aliphatic glycols, dihydroxy aromatics, bisphenols, and hydroxyl-terminated polyethers, polyesters, and polyacetals, among others. Extensive lists of suitable polyols may be found in the above references and in many patents, for example in columns 2 and 3 of U.S. Pat. No. 3,652,639, columns 2–6 of U.S. Pat. No. 4,421,872; and columns 4–6 of U.S. Pat. No. 4,310,632; these three patents being hereby incorporated by reference.

Preferably used are hydroxyl-terminated polyoxyalkylene polyols. The former are generally prepared by well known methods, for example by the base catalyzed addition of an alkylene oxide, preferably ethylene oxide (oxirane), propylene oxide (methyloxirane) or butylene oxide (ethyloxirane) to an initiator molecule containing on the average two or more active hydrogens. Examples of preferred initiator molecules are dihydric initiators such as ethylene glycol, propylene glycol, butylene glycol, neopentyl glycol, 1,6-hexanediol, hydroquinone, resorcinol, the bisphenols, aniline and other aromatic monoamines, aliphatic monoamines, and monoesters of gylcerine; trihydric initiators such as glycerine, trimethylolpropane, trimethylolethane, N-alkylphenylenediamines, mono-, di, and trialkanolamines; tetrahydric initiators such as ethylene diamine, propylene diamine, 2,4-, 2,2'- and 4,4'-methylenedianiline, toluenediamine, and pentaerythritol; pentahydric initiators such as diethylenetriamine; and hexahydric and octahydric initiators such as sorbitol and sucrose.

Addition of alkylene oxide to the initiator molecules may take place simultaneously or sequentially when more than one alkylene oxide is used, resulting in block, heteric, and block-heteric polyoxyalkylene polyethers.

The number of hydroxyl groups will generally equal the number of active hydrogens in the initiator molecule. Processes for preparing such polyethers are described both in the Polyurethane Handbook and Polyurethanes; Chemistry and Technology as well as in many patents, for example U.S. Pat. Nos. 1,922,451; 2,674,619; 1,922,459; 3,190,927; and 3,346,557.

Polyester polyols also represent polyurethane-forming reactants. Such polyesters are well known in the art and are prepared simply by polymerizing polycarboxylic acid derivatives, for example the corresponding acid chlorides or anhydrides, with a polyol. Numerous polycarboxylic acids are suitable, for example malonic acid, citric acid, succinic acid, glutaric acid, adipic acid, pimelic acid, azelaic acid, sebacic acid, maleic acid, fumaric acid, terephthalic acid, and phthalic acid. Numerous polyols are suitable, for example the various aliphatic glycols, trimethylolpropane and trimethylolethane, α-methylglucoside, and sorbitol. Also suitable are low molecular weight polyoxyalkylene glycols such as polyoxyethylene glycol, polyoxypropylene glycol, and block and heteric polyoxyethylene-polyoxypropylene glycols. These lists of dicarboxylic acids and polyols are illustrative only, and not limiting. An excess of polyol should be used to ensure hydroxyl termination. Methods of preparation of such polyester polyols are given in the Polyurethane Handbook and in Polyurethanes; Chemistry and Technology.

Illustrative polymerization initiators which may be employed are the well-known free radical types of vinyl polymerization initiators such as the peroxides, persulfates, perborates, percarbonates, azo compounds, etc. These include hydrogen peroxide, dibenzoyl peroxide, acetyl peroxide, benzoyl hydroperoxide, t-butyl hydroperoxide, di-t-butyl peroxide, lauroyl peroxide, butyryl peroxide, diisopropylbenzene hydroperoxide, cumene hydroperoxide, paramenthane hydroperoxide, diacetyl peroxide, di-o-cumyl peroxide, dipropyl peroxide, diisopropyl peroxide, isopropyl-t-butyl peroxide, butyl-t-butyl peroxide, difuroyl peroxide, bis(triphenylmethyl) peroxide, bis(p-methoxybenzoyl) peroxide, p-monomethoxybenzoyl peroxide, rubene peroxide, ascaridol, t-butyl peroxybenzoate, diethyl peroxyterephthalate, propyl hydroperoxide, t-butyl hydroperoxide, cyclohyexyl hydroperoxide, trans-decalin hydroperoxide, α-methylbenzyl hydroperoxide, α-methyl-α-ethyl benzyl hydroperoxide, tetralin hydroperoxide, triphenylmethyl hydroperoxide, diphenylmethyl hydroperoxide, α,α'-azobis-(2-methyl heptonitrile), 1-t-butylazo-1-cyanocyclohexane, persuccinic acid, diisopropyl peroxy discarbonate, 2,2'-azobis-(2-4-dimethylvaleronitrile), 2-t-butylazo-2-cyano-4-methoxy-4-methylpentane,2,2'-azo-bis-2-methylbutanenitrile, 2-t-butylazo-2-cyanobutane, 1-t-amylazo-l-cyanocyclohexane, 2,2'-azobis-2,4-dimethyl-4-methoxyvaleronitrile, 2,2'-azobis-2-methylbutyronitrile, 2-t-butylazo-2-cyano-4-methylpentane, 2-t-butylazo-2-isobutyronitrile, and the like; a mixture of initiators may also be used. The preferred initiators are 2,2'-azobis-2-methylbutyronitrile, 2,2'-azobis(isobutyronitrile), 2-2'-azobis(2,4-dimethylvaleronitrile), 2-t-butylazo-2-cyano-4-methoxy-4-methyl pentane, 2-t-butylazo-2-cyano-4-methylpentane, 2-t-butylazo-2-cyano-butane and lauroyl peroxide. Generally, from about 0.1 percent to about 10 percent, preferably from about 1 percent to about 4 percent, by weight of initiator based on the weight of the monomer will be employed in the process of the invention.

Any suitable catalyst or mixture of catalysts may be used including tertiary amines such as, for example, triethylenediamine, N-methylmorpholine, N-ethylmorpholine, diethylethanolamine, N-cocomorpholine, 1-methyl-4-dimethylamino-ethylpiperazine, 3-methoxypropyldimethylamine, N,N,N'-trimethylisopropyl propylenediamine, 3-diethylaminopropyldiethylamine, dimethylbenzylamine, and the like. Other suitable catalysts are, for example, stannous chloride, dibutylin-di-2-ethyl hexonate, potassium hexanoate, stannous oxide, as well as other organometallic compounds such as are disclosed in U.S. Pat. No. 2,846,408.

In some instances, a surface-active agent is necessary for production of polyurethane foam. Numerous surface-active agents have been found satisfactory. Of these, the nonionic surface-active agents such as the well known silicones have been found particularly desirable when use of a surfactant is necessary. Other surface-active agents which are operative, although not preferred, include polyethylene glycol ethers of long chain alcohols, tertiary amine or alkanol amine salts of long chain alkyl acid sulfate esters, alkyl sulfonic esters, and alkyl arylsulfonic acids. Use of a surfactant in the present invention is optional.

A chain extender and/or crosslinker is used as well in the present invention These include those compounds having at least two functional groups bearing active hydrogen atoms such as, hydrazine, primary and secondary diamines, amino alcohols, amine acids, hydroxy acids, glycols, or mixtures thereof. Glycerin is an example of a preferred compound used as a crosslinker.

Other optional additives which fall within the scope of the present invention include known pigments, such as carbon black, dyes, stabilizers against aging and weathering, fungistats, bacteriostats, fillers, or flame retarding agents.

The following examples serve to illustrate the present invention and are not considered limiting thereof.

Suitable methods of preparation include the prepolymer technique wherein an excess of organic polyisocyanate is reacted with a polyol to prepare a prepolymer having free isocyanate reactive groups, which is then reacted with a mixture of water, surfactant, aroma chemical, and catalyst to obtain foam. Another option is to prepare a foam by reacting all the components in a single working step known as the "one-shot" method. In the one-shot method, the components may be mixed in a mix head or by impingement mixing.

The polyurethane components combined by any one of the above-mentioned techniques may be poured or sprayed into an open mold, which is subsequently closed and clamped, if necessary, to allow the components to fully react, after which the part is demolded and allowed to cure. Alternatively, the polyurethane components may be injected into an open or closed mold, which is subsequently closed if the components were initially injected into an open mold; and the components are allowed to fully react after which the part is demolded and set aside to cure.

The mixed polyurethane components may also be poured, injected, or sprayed into open cavities or molds and allowed to free rise instead of reacting in a closed mold, such as in the production of slab stock which is cut into a desired shape, a pour-in-place method of applying rigid polyurethane between panels used as the final part, or a pour-behind method of foaming.

A typical polyurethane formulation is as follows:

60 parts by weight of an ethylene oxide-propylene oxide adduct of a mixture of vicinal toluene diamine and dipropylene glycol containing a polyoxypropylene polyether cap and having an hydroxyl number of 450 and is commercially available from BASF Corporation as Pluracol®1132 polyol.

35 parts by weight of a glycerine initiated all proylene oxide adduct having a theoretical hydroxyl number of 398 and is commercially available from BASF Corporation as Pluracol® GP 430 polyol.

5 parts by weight of diethylene glycol having a theoretical hydroxyl number of 1016.

6.79 parts by weight water 1.5 parts by weight tetramethylhexanediamine, a urethane-promoting catalyst.

1 part by weight of a silicone surfactant commercially available from Union Carbide.

231.9 parts by weight of ISO A, a solvent free polymethylene polyphenylisocyanate having a functionality of about 2.7 and an NCO content of about 31.8 weight percent.

The following aroma chemicals can be incorporated into a typical polyurethane formulation an explained above in the loading of 15% by weight of the total of the polyurethane forming components.

Andrane (8,9-epoxy cedrane)

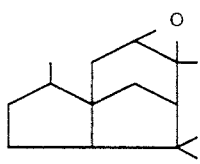

Benzyl Acetate

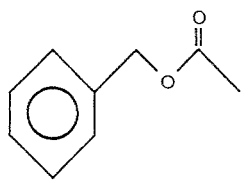

Benzyl Benzoate

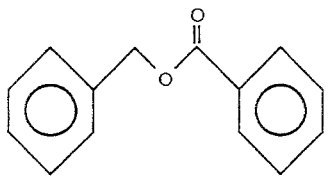

Citralva® (3,7-dimethyl-2,6-octadiene-1-nitrile)

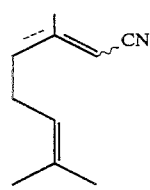

Diethyl phthalate (special odorless)

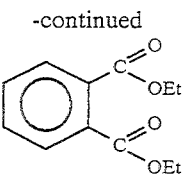

Diola (methyl n-hexyl ether)

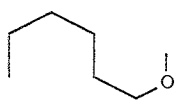

Dipropylene Glycol

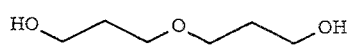

Ethyl Butyrate

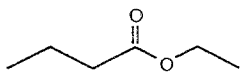

Ethyl Methyl Phenyl Glycidate

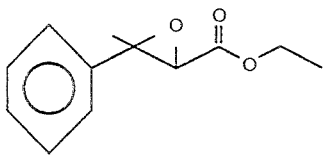

Eucalyptol USP

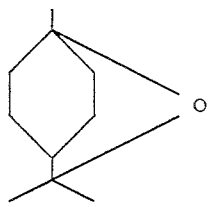

Eugenol (4-allyl-2-methoxy phenol)

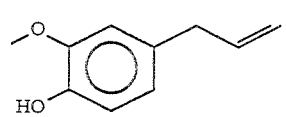

Fructone (ethyl-2-methyl-1,3-dioxolane-2-acetate)

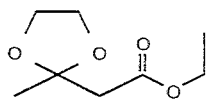

Geraniol RG (3,7-dimethyl-2,6-octadien-1-ol)

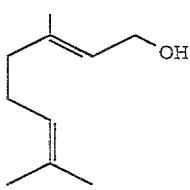

Cis-3-Hexenyl Salicylate

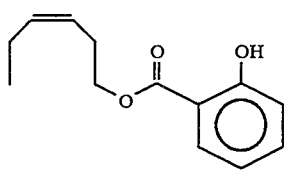

Hexyl Cinnamic Aldehyde

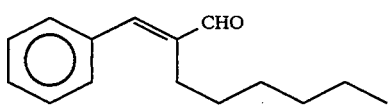

Iso E Super ® (7-acetyl,1,2,3,4,5,6,7,8-octahydro-1,1,6,7-tetra methyl naphthalene)

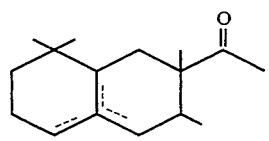

Kharismal

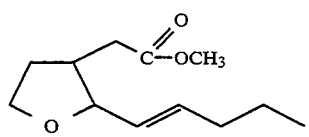

Kohinool ® (3,4,5,6,6-pentamethyl 2-heptanol)

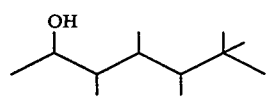

Koavone ® (acetyl diisoamylene)

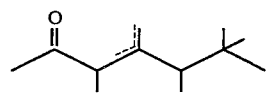

Lemsyn GB (3,7-dimethyl-2,6-octadien-1-al)

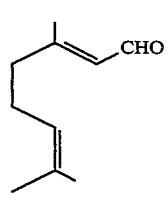

Lilial (para t-butyl α-methyl hydrocinnamic aldehyde)

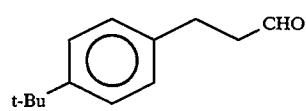

Limonene VAH (p-mentha-1,8-diene)

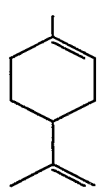

Lyral ® (4(4-hydroxy-4-methylpentyl) 3-cyclohexene-1-carboxaldehyde)

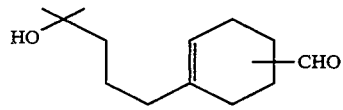

Methyl Anthranilate

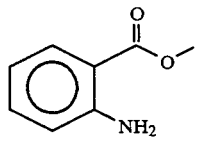

Methyl Lavender Ketone (3-(hydroxy methyl) 2-nonanone)

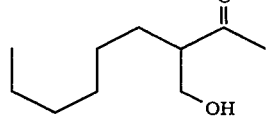

MUSQ ® 1-2-1

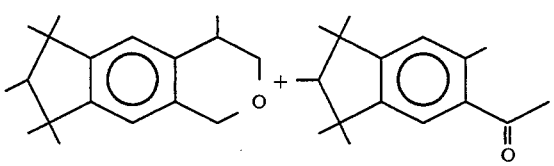

Peach aldehyde Coeur (gamma-undecalactone)

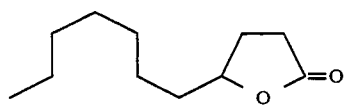

Phenafleur ® (cyclohexyl phenethyl ether)

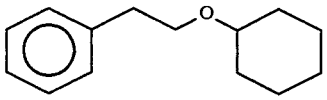

Phenoxanol ® (3-methyl-5-phenyl 1-pentanol)

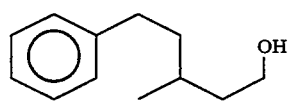

Prismantol

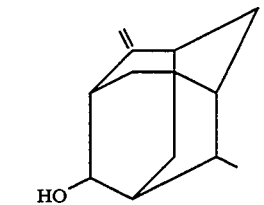

Sanjinol ™

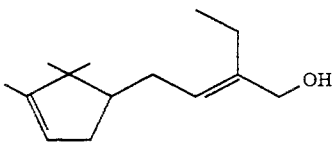

Tetrahydro muguol coeur (3,7-dimethyl-3-octanol and 2,6-dimethyl-2-octanol)

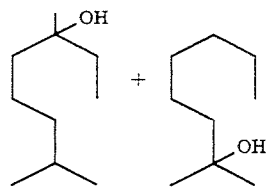

Tabacarol

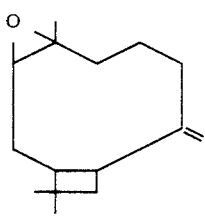

By preparing a polyurethane foam of a given polyol/isocyanate formulation with each aroma chemical and then measuring hardness of the resulting foam, it is possible to prepare a chart or panel of values providing an indication of relative hardness keyed to structure of the aroma chemical. Therefore, choosing any one of the above fragrances and a suitable polyisocyanate/polyol combination enables one to make a fragrant polyurethane foam. Based on a range of 1 to 10, the following chart shows the relative hardness of the products obtained in accordance with the present invention. Hardness can be measured by instrument or manually as is known in the art.

| Aroma Chemical | Molecular weight | Polarity | Hardness of Foam |
|---|---|---|---|
| Andrane | 220 | 1 | 4 |
| Benzyl acetate | 150 | 2 | 3 |
| Benzyl benzoate | 212 | 9 | 9 |
| Citralva ® | 149 | 2 | 5 |
| Diethyl phthalate | 126 | 2 | 10 |
| Diola | 116 | 2 | 10 |
| Dipropylene glycol | 150 | 8 | 1 |
| Ethyl butyrate | 116 | 6 | 7 |
| Ethyl methyl phenyl Glycolate | 202 | 2 | 1 |
| Eucalyptol USP | 154 | 3 | 6 |
| Eugenol | 164 | 7 | 5 |
| Fructone | 174 | 6 | 5 |
| Geraniol RG | 154 | 4 | 2 |
| cis-3 Hexenyl salicylate | 220 | 2 | 4 |
| Hexyl cinnamic aldehyde | 216 | 4 | 8 |
| ISO E Super ® | 234 | 3 | 4 |
| Kharismal | 200 | 2 | 4 |
| Kohinool ® | 186 | 4 | 7 |
| Koavone ® | 182 | 6 | 4 |
| Lemsyn GB | 152 | 9 | 4 |
| Lilial | 190 | 3 | 8 |
| Limonene VAH | 136 | 2 | 10 |
| Lyral ® | 210 | 3 | 1 |
| Methyl anthranilate | 151 | 9 | 5 |
| Methyl Lavender Ketone | 172 | 9 | 2 |
| MUSQ 1-2-1 ® | 258 | 3 | 8 |
| Peach Aldehyde Coeur | 184 | 5 | 2 |
| Phenafleur ® | 204 | 3 | 9 |
| Phenoxanol ® | 178 | 7 | 2 |
| Prismantol | 178 | 4 | 2 |
| Sanjinol ™ | 186 | 4 | 6 |
| Tetrahydro muguol Coeur | 158 | 3 | 5 |
| Tabacarol | 218 | 5 | 5 |

In making the fragrant polyurethane foams of the present invention one first selects suitable polyols and polyisocyanates for reaction to make a foam having the characteristics that would be predictable based on the knowledge in the prior art of the expected properties of a polyurethane foam made from such ingredients. These general parameters are well known in the art and persons skilled in the art would be able to predict the general characteristics of the resulting polyurethane foam depending upon the polyol and polyisocyanate that was chosen. The aroma chemical is then chosen and introduced in an amount which may range from 5 to 20% by weight, preferably 15%, of the total ingredients. The type of aroma chemicals selected and therefore the nature of the final properties of the product can be determined by routine experimentation and by calculation using the empirical formula described below. It is possible to specify in advance what the final general nature of the foam product will be depending upon the aroma chemical that is selected. By making a series of foams employing selected aroma compounds and using the same basic foam formulation, it is then possible to establish a table according to the chemical structure of the aroma compound correlating hardness obtained with the specific aroma compound. Thereafter, the skilled worker can then make a selection of an aroma chemical from that table for combination with and introduction into any other polyol and polyisocyanate formulation for foam production whereby the general degree of hardness of the final polyurethane foam could be predicted.

As will be apparent, the polyurethanes produced in accordance with the present invention can be molded into any shape or configuration as is the case with other polyurethane formulations.

To control and thereby determine the hardness of the resulting polyurethane foam the following empirical formula can be used to obtain an approximation of relative hardness for a given aroma chemical $$\log_e(Z) = 1.87(X/Y)^{0.27}$$

wherein

Z = hardness of foam
X = polarity of aroma chemical
Y = actual molecular weight of aroma chemical As a first step after choosing a particular aroma chemical and determining its actual molecular weight, it is necessary to establish a value for the polarity of the molecule based on a scale of 1 to 10. The above table of representative aroma chemicals provides ample guidelines for persons skilled in the art to establish a value for polarity of selected aroma chemicals based on their known structure in comparison to known chemicals for which a polarity value is set forth above. Then using the above formula, an approximate relative hardness can be calculated whereby a value will be arrived at ranging from 1 to 10 and can be compared to the above list.

In lieu of using the formula, a series of experiments can also be carried out as described above to prepare a table of representative data.

Further variations and modifications of the foregoing will be apparent to those persons skilled in the art and are intended to be encompassed by the claims appended hereto.

I claim:

1. A method for determining the hardness of a fragrance containing polyurethane foam comprising, selecting an aroma chemical, determining the molecular weight thereof, assessing a polarity to said aroma chemical based on a range of 1 to 10 where adrane has a polarity of 1 and benzyl benzoate has a polarity of 9, calculating the hardness of the resulting polyurethane foam by using the empirical formula:

$$\log_e(Z) = 1.87(X/Y)^{0.27}$$

wherein

Z in the hardness of the resulting foam on a scale of 1 to 10, X is the polarity of the aroma chemical on a scale of 1 to 10, and Y is the actual molecular weight of the aroma chemical, introducing the selected aroma chemical into a reaction mixture including an organic polyisocyanate and a hydroxy compound, reacting the reaction mixture to thereby form the polyurethane foam according to the desired hardness to be obtained.

2. A method as defined in claim 1 wherein the aroma chemical is selected from the group consisting of the following with the assessed polarity indicated:

andrane 1, benzyl acetate 2, benzyl benzoate 9, geranonitrile 2, diethyl phthalate 2, diola 2, dipropylene glycol 8, ethyl butyrate 6, ethyl methyl phenyl glycolate 2, eucalyptol 3, eugenol 7, fructone 6, geraniol 4, cis-3-hexenyl salicylate 2, hexyl cinnamic aldehyde 4, -7acetyl,1,2,3,4,5,6,7,8-octahydro-1,1,6,7-tetramethyl naphthalene 3, kharismal 2, 3,4,5,6,6-pentamethyl 2-heptanol 4, acetyl diisoamylene 6, lemsyn 9, lilial 3, limonene 2, Lyral® 3, methyl anthranilate 9, methyl lavender ketone 9, MUSQ-1-2-1® 3, peach aldehyde coeur 5, cyclohexyl phenethyl ether 3, 3-methyl-5-phenyl 1-pentanol 7, prismantol 4, Sanjinol ™ 4, tetrahydro muguol coeur 3, and tabacarol 5.

3. The method according to claim 2 wherein the aroma chemical is present in the amount of 15% by weight.

4. A method according to claim 2 wherein the polyurethane foam is produced from a polyisocyanate and polyol reactant mixture.

5. The method according to claim 2 further comprising preparing a table containing a list of aroma chemicals, determining a relative polarity of each of said aroma chemicals based on the known chemical structure thereof on a scale of 1 to 10, determining the molecular weight of said aroma chemical and calculating according to said empirical formula to establish a hardness value for each of the aroma chemicals on said list, and thereafter selecting an aroma chemical from said list for incorporating into said reaction mixture to obtain a foam having a predictable hardness on a scale of 1 to 10.

6. A method for determining the hardening of fragrance containing polyurethane foams based on the selection of the fragrance imparting aroma chemicals comprising selecting a plurality of aroma chemicals ranging in polarity from 1 to 10, based on a scale of 10 where adrane has a polarity of 1 and benzyl benzoate has a polarity of 9, introducing each one of said selected aroma chemicals in a polyurethane forming reaction mixture of identical formulation, carrying out a separate reaction to produce a separate polyurethane foam for each of said aroma chemicals selected, measuring the hardness value of the respective foams produced thereby and establishing values based on a scale of 1 to 10 from soft to most hard, preparing a table correlating aroma chemical, polarity and hardness as a standard and thereafter using said standard for purposes of selecting other aroma chemicals for incorporation into polyurethane foam forming reaction mixtures, to thereby enable the selection of an aroma chemical based on polarity for incorporation into said reaction mixture and determining the hardness of the resulting foam according to the equation:

$$\log_e(Z) = 1.87(X/Y)^{0.27}$$

wherein

Z is the approximate hardness of the foam on a scale of 1 to 10, X is the polarity of the aroma chemical on a scale of 1 to 10 and Y is the actual molecular weight of the aroma chemical.

* * * * *